US00PP10882P

United States Patent [19]

Walden

[11] Patent Number: Plant 10,882

[45] Date of Patent: May 4, 1999

[54] MINIATURE ROSE PLANT NAMED 'JACORCA'

[75] Inventor: John K. Walden, Thousand Oaks, Calif.

[73] Assignee: Bear Creek Gardens, Inc., Medford, Oreg.

[21] Appl. No.: 08/997,099

[22] Filed: Dec. 23, 1997

[51] Int. Cl.[6] ..... A01H 5/00

[52] U.S. Cl. ..... Plt./116

[58] Field of Search ..... Plt./116, 12

*Primary Examiner*—Howard J. Locker

*Attorney, Agent, or Firm*—Klarquist Sparkman Campbel Leigh & Whinston, LLP

[57] ABSTRACT

Miniature rose plant having flower color of coral orange with a light yellow cream reverse; a compact, miniature rose habit; dark green, glossy foliage having resistance to powdery mildew and rust; high centered, pointed ovoid bud form; and high petal substance.

1 Drawing Sheet

1

The present invention relates to a new and distinct variety of rose plant of the miniature class which was originated by me by crossing an unnamed seedling (cross of 'JACfun' and 'MORgal'), with the variety 'JACship' (U.S. Plant Pat. No. 7948).

The primary objective of this breeding was to produce a new rose variety having the bicolor flower, flower form and foliage of the unnamed female parent, the foliage characteristics of the male parent, the disease resistance of both parents, and a compact, miniature habit smaller than either parent. The objective was substantially achieved, along with other desirable improvements, as evidenced by the following unique combination of characteristics that are outstanding in the new variety and that distinguish it from its parents, as well as from all other varieties of which I am aware:

1. Flower color of coral orange with a light yellow cream petal reverse;
2. Compact, miniature rose habit;
3. Resistance to powdery mildew and rust;
4. Dark green, glossy foliage;
5. High-centered, pointed ovoid bud form; and
6. High petal substance.

Asexual reproduction of this new variety by hardwood cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—'JACship' (U.S. Plant Pat. No. 7,948).

Classification:

*Botanical.*—Rosa hybrida.

*Commercial.*—Miniature rose.

Flower

Observations made from specimens grown in a garden environment at Somis, Calif., Nov. 17, 1997.

2

Blooming habit: Continuous.

*Size*—Five-eighths inch long when the petals start to unfurl.

*Form.*—The bud form is pointed ovoid.

*Color.*—When sepals first divide, bud color is predominantly Orange-Red Group 34A. When half blown, the upper sides of the petals are Orange-Red Group 33A; and the lower sides of the petals are predominantly Yellow Group 16D blended with Orange-Red Group 33A.

*Sepals.*—Color: Green group 143C with tones of Greyed-Purple Group 183B. Surface texture: Smooth, glabrous. There are three heavily appendaged sepals. There are two unappendaged sepals with hairy edges.

*Receptacle.*—Color: Green group 143C and Greyed-purple group 183B. Shape: Pear. Size: Medium (5/16"×1/4"). Surface: Smooth to slightly hairy.

*Peduncle.*—Length: Long (1½"). Surface: Smooth. Color: Light green and bronzy. Strength: Stiff, erect.

Bloom:

*Size.*—Small Average open size is 1½ to 1¾ inches.

*Borne.*—Singly and several together.

*Stems.*—Short (6"–8").

*Form.*—When first open: High centered. Permanence: All petals curl, moderately quill fashion.

*Petalage.*—Number of petals under normal conditions: 30–35.

*Color.*—The upper sides of the petals are Red Group 43A on outer one-third changing to Red Group 37B. The reverse sides of the petals are predominantly Yellow-Orange Group 19D with some Red Group 43A near petal margins. The base of each petal has a half moon that is near Yellow Group 8B. The major color on the upper side is Red Group 43A.

*Variegations.*—None.

*Discoloration.*—The general tonality at the end of the first day is Red Group 43A; and at the end of the third day: Red Group 44C and Red Group 44D.

*Fragrance.*—None.

Petals:

*Texture.*—Leathery.

*Shape.*—Deltoid.

*Form.*—Edges slightly quilled.

*Arrangement.*—Imbricated (regularly arranged). Petaloids in the center are few and small.

*Persistence.*—Drop off cleanly before drying.

*Lastingness.*—On the plant: Long (eight to ten days). As a cut flower: Long (eight to ten days).

eproductive parts:

*Anthers.*—Size: Medium. Quantity: Many. Color: Near yellow-orange group 15C. Arrangement: Regular around styles

*Filaments.*—Color: Yellow Group 11B.

*Pollen.*—Color: Yellow-Orange Group 16A.

*Styles.*—Color: Red Group 47C.

*Stigmas.*—Color: Greenish-white.

lant:

*Form.*—Bush, miniature.

*Growth.*—Very vigorous; upright; branching; Height at one year in Somis, Calif. is 22" to 24" while the width is 18" to 20".

oliage: Number of leaflets on normal mid-stem leaves: Five.

*Size.*—Small (2⅞"long×1⅝" wide).

*Quantity.*—Normal.

*Color.*—New foliage: Reddish, changing rapidly to green. Upper and lower surfaces: Red Group 46A. Old foliage: Dark green, glossy. Upper surface: Between Green Group 137A and Green Group 139A. Lower surface: Green Group 137C.

*Shape.*—Pointed oval.

*Texture.*—Upper side: Glossy.

*Edge.*—Serrated.

*Serration.*—Mostly single.

*Petiole rachis.*—Color: Green (yellow-green) group; 146B).

*Petiols underside.*—With prickles.

*Stipules.*—Medium (3/16" to ¼"); serrated.

*Disease resistance.*—Resistant to mildew and rust under normal growing conditions at Somis and Wasco, Calif.

Wood:

*New wood.*—Color: Reddish, changing rapidly to light green. Bark: Smooth.

*Old wood.*—Color: Green, near yellow-green. Group 146B. Bark: Smooth.

Prickles:

*Quantity.*—On main canes from base: Ordinary to few. On laterals from main canes: Ordinary to few.

*Form.*—Short; angled downward.

*Color when young.*—Green and red.

Small prickles:

*Quantity.*—On main stalks: None. On laterals: None.

I claim:

1. A new and distant variety of miniature rose plant as herein shown and described, characterized particularly as to novelty by its flower color of coral orange with a light yellow cream reverse; a compact, miniature rose habit; dark green, glossy foliage having resistance to powdery mildew and rust; high centered, pointed ovoid bud form; and high petal substance.

* * * * *

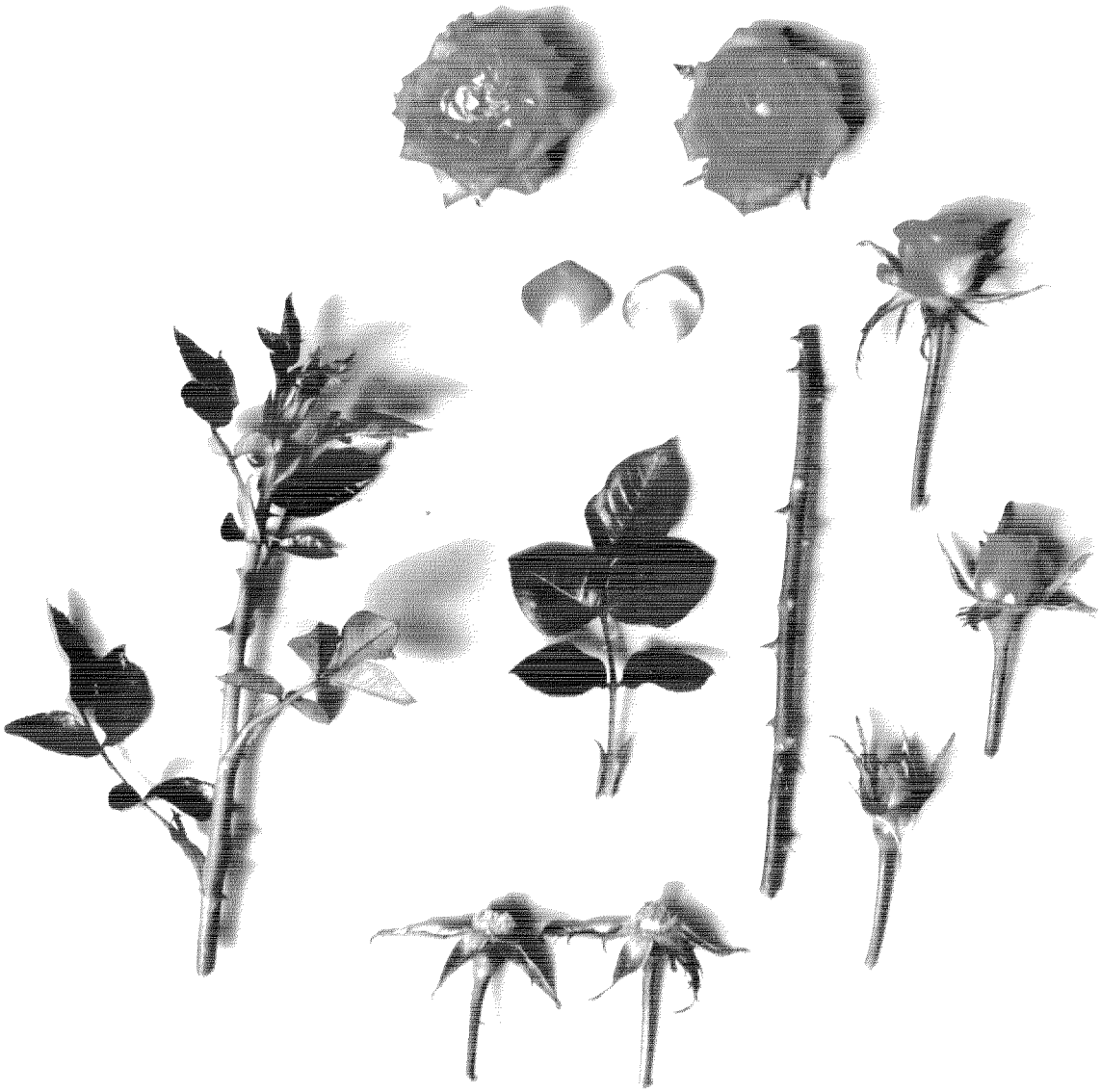
JACorea

UNITED STATES PATENT AND TRADEMARK OFFICE

CERTIFICATE OF CORRECTION

PATENT NO. : PP 10,882
DATED : May 4, 1999
INVENTOR(S) : John K. Walden

It is certified that error appears in the above-identified patent and that said Letters Patent is hereby corrected as shown below:

Column 2,
Line 2, insert -- Bud: -- before "Size".

Signed and Sealed this

Thirteenth Day of January, 2004

JON W. DUDAS
*Acting Director of the United States Patent and Trademark Office*